United States Patent
Goo et al.

(10) Patent No.: US 9,763,878 B2
(45) Date of Patent: Sep. 19, 2017

(54) MICROGRANULAR FORMULATION INCLUDING COAGULATION UNIT COMPRISING DISCONTINUOUS PHASE AND CONTINUOUS PHASE

(71) Applicants: CorePharm Co., Ltd., Gyeonggi-do (KR); CorePharmbio Co., Ltd., Gyeonggi-do (KR)

(72) Inventors: Young Sam Goo, Chungcheongbuk-do (KR); Jeong Tae Kim, Seoul (KR)

(73) Assignees: COREPHARM CO., LTD., Gyeonggi-Do (KR); COREPHARMBIO CO., LTD., Gyeonggi-Do (KR)

( * ) Notice: Subject to any disclaimer, the term of this patent is extended or adjusted under 35 U.S.C. 154(b) by 0 days.

(21) Appl. No.: 14/758,486

(22) PCT Filed: Dec. 27, 2013

(86) PCT No.: PCT/KR2013/012351
§ 371 (c)(1),
(2) Date: Jun. 29, 2015

(87) PCT Pub. No.: WO2014/104844
PCT Pub. Date: Jul. 3, 2014

(65) Prior Publication Data
US 2015/0352043 A1 Dec. 10, 2015

(30) Foreign Application Priority Data
Dec. 31, 2012 (KR) .................. 10-2012-0158630

(51) Int. Cl.
*A61K 47/00* (2006.01)
*A61K 9/00* (2006.01)
(Continued)

(52) U.S. Cl.
CPC .......... *A61K 9/0056* (2013.01); *A61K 9/1623* (2013.01); *A61K 9/1682* (2013.01);
(Continued)

(58) Field of Classification Search
CPC .. A61K 9/0056; A61K 9/1623; A61K 9/1682; A61K 45/06; A61K 31/4178;
(Continued)

(56) References Cited

U.S. PATENT DOCUMENTS

| 5,837,285 A | * | 11/1998 | Nakamichi | .......... A61K 9/2095 424/435 |
|---|---|---|---|---|
| 2012/0237602 A1 | | 9/2012 | Ikeda et al. | .................... 424/480 |
| 2013/0224295 A1 | | 8/2013 | Miyamoto et al. | .......... 424/465 |

FOREIGN PATENT DOCUMENTS

| JP | 2011-063627 | 3/2011 |
|---|---|---|
| KR | 10-2006-0129106 | 12/2006 |

OTHER PUBLICATIONS

Drooge et al, Incorporation of Lipophilic Drugs in Sugar Glasses by Lyophilization using a Mixtures of Water and Tertiary Butyl Alcohol as Solvent, Journal of Pharmaceutical Sciences , vol. , 93, No. 3, Mar. 2004, p. 713-725.*

(Continued)

*Primary Examiner* — T. Victor Oh
(74) *Attorney, Agent, or Firm* — Harness, Dickey & Pierce, P.L.C.

(57) ABSTRACT

A pharmaceutical composition which is Rapidly Dissolved in a mouth, comprising
(a) agglomerate units which is consisted of a discontinuous phase comprising the first component; and a continuous phase comprising the second component; and
(b) a pharmaceutically acceptable excipient,
in which the pharmaceutical composition is characterized in that the first component is an effective ingredient (Continued)

Extent of Experiment 1:
bitterness Estimation for masking the high bitterness

A : Hydrochloric acid donepezil
B : Udenafil
C : Citric acid sildenafil
D : Hydrochloric acid vadenafil
E : Succinic acid sumatriptan
F : Hydrochloric acid dapoxetin
G : Hydrochloric acid ondansetron exhibiting the pharmacological activity, and the second component is sugar or sugar alcohol is provided.

4 Claims, 4 Drawing Sheets

(51) Int. Cl.
*A61K 9/16* (2006.01)
*A61K 45/06* (2006.01)
*A61K 31/047* (2006.01)
*A61K 31/138* (2006.01)
*A61K 31/4045* (2006.01)
*A61K 31/4178* (2006.01)
*A61K 31/445* (2006.01)
*A61K 31/519* (2006.01)
*A61K 31/53* (2006.01)

(52) U.S. Cl.
CPC .......... *A61K 31/047* (2013.01); *A61K 31/138* (2013.01); *A61K 31/4045* (2013.01); *A61K 31/4178* (2013.01); *A61K 31/445* (2013.01); *A61K 31/519* (2013.01); *A61K 31/53* (2013.01); *A61K 45/06* (2013.01)

(58) Field of Classification Search
CPC .. A61K 31/138; A61K 31/445; A61K 31/519; A61K 31/047; A61K 31/4045; A61K 31/53
USPC .................................. 540/451; 514/772, 784
See application file for complete search history.

(56) References Cited

OTHER PUBLICATIONS

Yourong (2004). Orally fast disintegrating tablets: developments, technologies, taste-masking and clinical studies. *Critical Review in Therapeutic Drug Carrier Systems*, 21(6):433-475.
International Search Report (ISR) in PCT/KR2013/012351, dated Apr. 15, 2014.

* cited by examiner

A : Hydrochloric acid donepezil
B : Udenafil
C : Citric acid sildenafil
D : Hydrochloric acid vadenafil
E : Succinic acid sumatriptan
F : Hydrochloric acid dapoxetin
G : Hydrochloric acid ondansetron A : Hydrochloric acid donepezil
B : Udenafil
C : Citric acid sildenafil
D : Hydrochloric acid vadenafil
E : Succinic acid sumatriptan
F : Hydrochloric acid dapoxetin
G : Hydrochloric acid ondansetron A : Hydrochloric acid donepezil
B : Udenafil
C : Citric acid sildenafil
D : Hydrochloric acid vadenafil
E : Succinic acid sumatriptan
F : Hydrochloric acid dapoxetin
G : Hydrochloric acid ondansetron A : Hydrochloric acid donepezil
B : Udenafil
C : Citric acid sildenafil
D : Hydrochloric acid vadenafil
E : Succinic acid sumatriptan
F : Hydrochloric acid dapoxetin
G : Hydrochloric acid ondansetron

MICROGRANULAR FORMULATION INCLUDING COAGULATION UNIT COMPRISING DISCONTINUOUS PHASE AND CONTINUOUS PHASE

CROSS-REFERENCE TO RELATED APPLICATIONS

This application is a national phase application of PCT Application No. PCT/KR2013/012351, filed on Dec. 27, 2013, which claims the benefit and priority to Korean Patent Application No. 10-2012-0158630, filed Dec. 31, 2012. The entire disclosures of the applications identified in this paragraph are incorporated herein by references.

FIELD

The present invention relates to a microgranule preparation which can be taken without water, and rapidly dissolved in a mouth when administering it orally. More specifically, the present invention relates to a microgranule preparation comprising an agglomerate unit which has the first component consisting of a main component with a bitter taste to mask a high bitterness as a discontinuous phase, and the second component consisting of sugar or sugar alcohol as a continuous phase. The microgranule preparation of the present invention has characteristics that it does not have any feeling of irritation and aftersensation in a mouth, when orally administering, furthermore it can be rapidly degraded and dissolved in the mouth.

BACKGROUND

Orodispersible tablet (ODT), orodispersible film (ODF) or oral disgrading powder is referred as an alternative administration preparation which can be administrated to a patient who is difficult to administer with a customary tablet or capsule, for example, an older patient or patient who represents a disphagia. Meanwhile, in the case of such special preparations, there are a lot of limitations in applying the special effective ingredients to it due to their inherent properties. For example, in the case of orodispersible film, there are problems that the amount of the effective ingredient which can be loaded on it is limited or the means for masking bitterness is not available to apply the drug with bitterness to it, and in the case of orodispersible tablet also has a limitation that it is difficult to apply to the drug with bitterness. Likewise, in the case of the powder, when the amount of the effective ingredient is higher, the one dose is too much and thus there is a difficulty to administer it. Also, in the case of the drug with bitterness, any separate means for masking the bitterness is needed, for example, when an inclusion compound with cyclodextrin, etc., is used, a unit cost of production is increased. Therefore, it is difficult to say that it is a proper industrial solution applicable to the real industrial site.

In particular, in the case of ODT or ODF, various means for masking the bitterness are already known in the art, but in the case of a powder, the means for masking the bitterness specialized to the powder has not developed until now in making the drug with the bitterness into the powder.

Technical Problem

Accordingly, the technical problem of the present invention is to provide a technical means for achieving the superior effects for masking the bitterness, with a relatively simple process, in preparing the drug with bitterness into a powder, as well as to provide a new powder preparation in which its disintegrating time in a mouth is very short and also does not have feelings of irritation and aftersensation in the mouth (since it has not been known in the relevant art until now, it is referred to 'microgranule preparation' in the present application).

Technical Solution

To accomplish the above-mentioned object, according to the present invention, there is provided a technical means as follows:

That is, a pharmaceutical composition which is rapidly dissolved in a mouth, which is characterized in comprising
(a) agglomerate units which is consisted of a discontinuous phase comprising the first component; and a continuous phase comprising the second component; and
(b) a pharmaceutically acceptable excipient,
in which the first component is an effective ingredient exhibiting the pharmacological activity, and the second component is sugar or sugar alcohol.

In addition, there is provided a pharmaceutical composition characterized in that the second component is selected from the group consisting of xylitol, mannitol, isomalt, sorbitol, maltitol, refined white sugar, lactose, inositol, erythritol, crystal fructose, trehalose, ribitol, arabitol, galatitol, lactitol and maltotritol.

Furthermore, in said pharmaceutical composition, there is provided a pharmaceutical composition which is characterized in additionally comprising a high sweetening agent.

Further, there is a pharmaceutical composition, which is characterized that the said high sweetening agent is present within the continuous phase.

Furthermore, there is provided a pharmaceutical composition which is characterized in that the said high sweetening agent is selected from a group consisting of sucrose, dextrose, fructose, glucose, liquid glucose, maltose saccharin, cyclamate, aspartame, acesulpham K, sucralose, alitame and neotame.

Furthermore, there is provided a preparation method which is characterized in that it comprises:
(a) a step for dissolving all or a part of the second component in a solvent;
(b) a step for obtaining a dispersion by dispersing the first component in the said solvent; and
(c) a step for obtaining an agglomerate unit by drying the said solvent.

Furthermore, there is provided a preparation method which is characterized in using no binding agent in obtaining the agglomerate unit.

Furthermore, there is provided a preparation method which is characterized in that the (a) step comprises dissolving the second component with the high sweetening agent in the solvent.

Advantageous Effects

According to the present invention, there can be provided a microgranule preparation which can be orally administered and is rapidly disintegrated in a mouth when orally administering unlike the general powder or granular preparation already known in the art, and the microgranule preparation has the superior effects for making bitterness of the drug and has no feelings of irritation and aftersensation in a mouth, after administering.

BEST MODE FOR INVENTION

Figure 1:
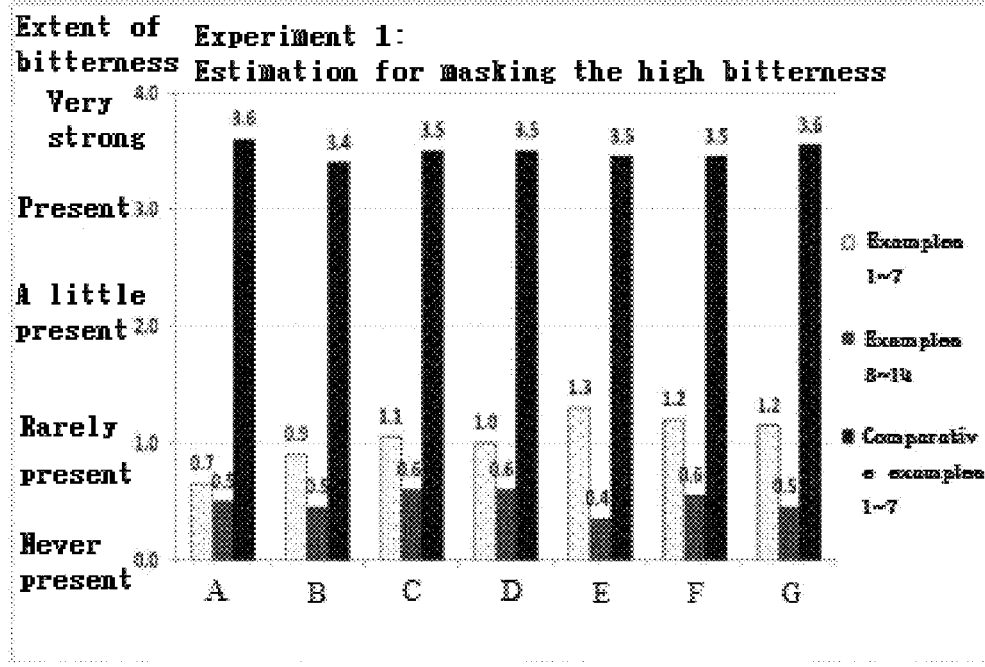
FIG. 1 represents an evaluation result for the masking effect of bitterness.
Figure 2:
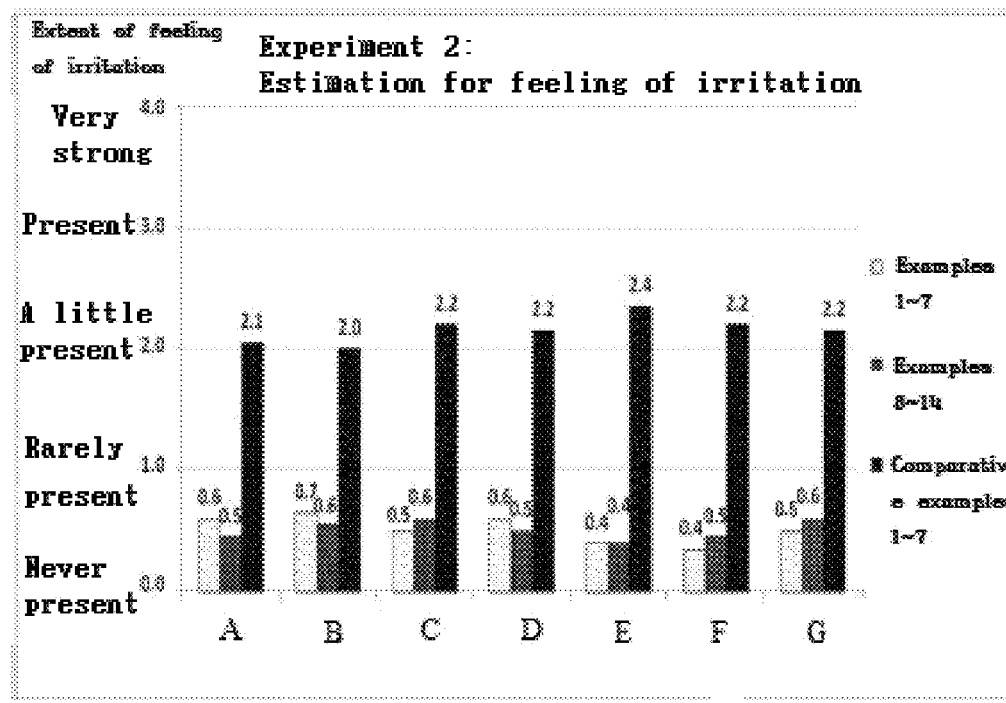
FIG. 2 represents an evaluation result for the feelings of irritation.
Figure 3:
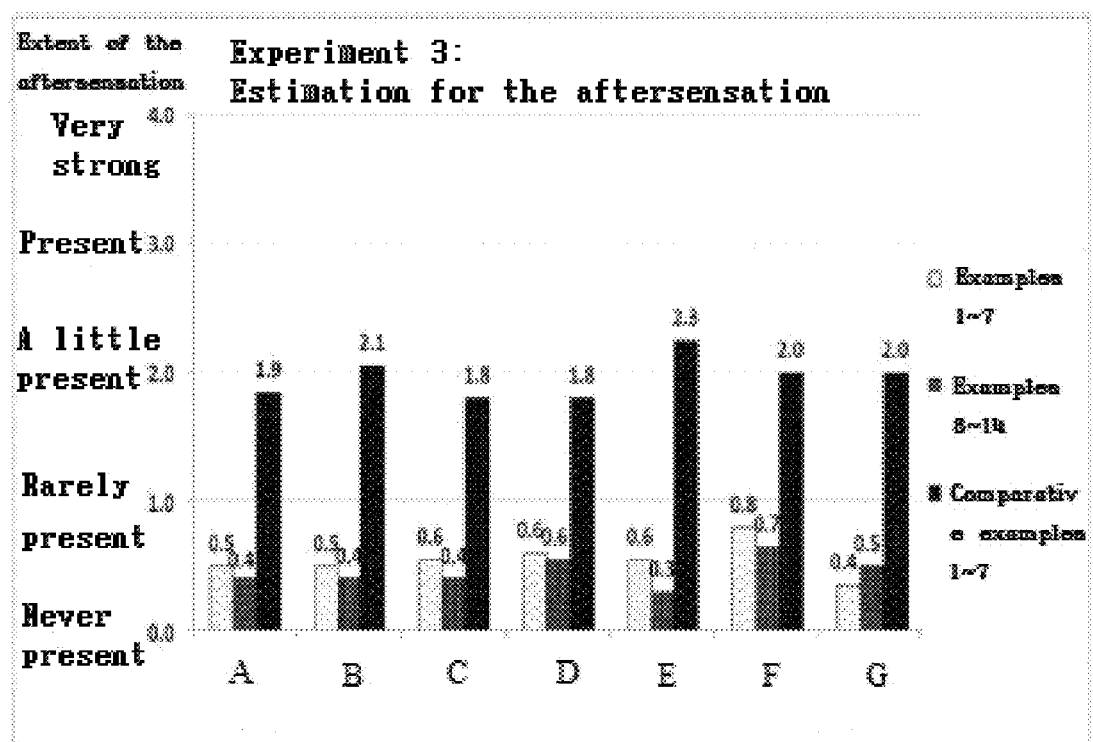
FIG. 3 represents an evaluation result for the aftersensation.
Figure 4:
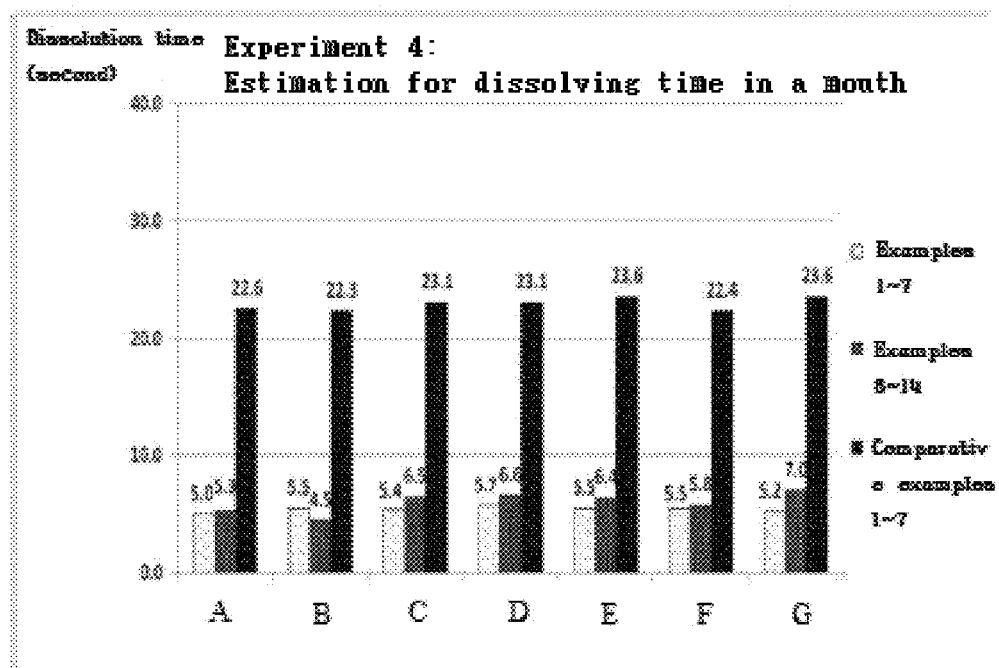
FIG. 4 represents an evaluation result for the dissolution time in a mouth.

Hereinafter, terms used in the present specification are defined.

'Microgranule preparation' as used in the present specification is used as having a common meanings comprising all of powder, microgranule and granule preparations defined in the Korean pharmacopoeia, but is not limited into them, and refers to the preparation having a granular form made of small fine or common granule.

Especially, the microgranule preparation of the present invention does not use a binding agent as used in the procedure assembling it with an ordinary common dry process or wet process, and also, means an assembly of an agglomerate unit consisting of a continuous and discontinuous phase by adopting the special preparation method.

'Agglomerate unit' of the present invention means a state in which effective ingredients agglomerate and contact with pharmaceutical acceptable excipients or additives by a physical binding.

'Discontinuous phase' of the present invention represents an embodiments in which the first component which is one element composing the agglomerate unit is present in the agglomerate unit, and means the form which is separately present by totally being surrounded by the second component within the agglomerate unit.

'Continuous phase' of the present invention represents an embodiment in which the second component which is another element composing the agglomerate unit is present in the agglomerate unit, and means the form which allows the first component to be present as discontinuous phase.

'Drug' of the present invention is included in the preparation of the present invention, and comprises a drug with bitterness, as a pharmacological active effective ingredient. Since the present invention is merely based on the fact that effective components can be included in the preparation of the invention, as the invention characterized in the preparation itself, such effective ingredients are not limited. Only that for example, the effective ingredients included in the present invention can be mentioned as sildenafil, tadalafil, udenafil, donepezil, glymeperid, dexybupropen, acetaminopen, pitavastatin, rebamipid, azythromycin, desmopressin, pranlukast, hydrochloric acid pseudoephedrine, hydrochloric acid ranitidine, hydrochloric acid rebocetirizine, etc., and comprise the pharmaceutical acceptable salts thereof.

'Sugar or sugar alcohol' as used in the present invention refers to the carrier which can be rapidly dissolved when orally administering it, and can constitute the continuous phase through the process for preparation of the present invention, as being an element for constituting the second component. As the specific example thereof, the pharmaceutical acceptable sugar or sugar alcohol and a mixture thereof, such as xylitol, manitol, isomalt, sorbitol, maltitol, the fined white sugar, lactose, inositol, erythritol, a crystal fructose, trehalose, ribitol, arabitol, galatitol, lactitol and maltotritol, etc. can be mentioned, but are not limited to them.

The feelings of irritation as used in the present specification refers to the feelings to which patient taken a medicine causes uncomfortableness due to that the patient notices it as a foreign substance and comprises, for example, a frickly feeling such as a sand, or a feeling irritating a mucosa of a mouth or tongue, and also a sticky feeling such as a mucus substance.

An aftersensation as used in the present specification means that although substantial amount of time has passed after administering the preparation, for example, about 20 seconds has passed after orally administering, and then the preparation comprising the effective ingredients has already dissolved and absorbed into the body, the sensation that a preparation or a part of it is remained in the mouth or the sensation related to a trace of taking the medicine such as a taste or feeling for the preparation is not yet removed in the mouth is maintained within the mouth, and means the sensation causing displeasure according to the patient, although it does not correspond to the feeling of irritation. When such aftersensation is present, it can result a desire to further drink water or a drink, and in this case, since the feature of the preparation characterized in taking it without water is not effected, it must be considered to improve the quality of the preparation together with the feeling of irritation.

Hereinafter, the present invention will be specifically explained.

When the effective ingredients are prepared in the form of powder or granule and then are administered, various limitations such as a dosage, a presence for aftersensation or feeling of irritation within a mouth, masking of bitterness, etc., are present. Among these, regarding the means for masking of bitterness, a method in which common sweetening agent is included in the preparation is classical, but according to the drug, it is not impossible to effectively mask the bitterness only with a sweetening agent. Therefore, methods using alkaline agent to adjust solubility by changing pH of the effective ingredients, or using an inclusion complex, or coating the effective ingredients by the polymer, etc. are considered as a means for masking bitterness, such methods are easily to destroy the characteristic features which are essential parts, that is, there is no aftersensation or feeling of irritation within the mouth, and also it should be rapidly dissolved in the mouth. Meanwhile, in the case of microgranule preparation of the present invention, inventors of the present application considered that since a residence time of the preparation presented in the mouth ranges from in short several minute to at length less than about 20~30 minutes, the preparation is instantaneously dissolved within such a short time and then moved into a gastrointestinal tract, and thus, when the masking means so as not to represent the bitterness are provided during staying it within the mouth, the patient can not feel the bitterness and then completed the present invention.

That is, the present invention is characterized in that the masking bitterness is made by controlling the internal structure of the agglomerate unit, unlike the traditional trials that the bitterness of the effective ingredients is masked by chemical methods.

More specifically, the agglomerate unit of the present invention is consisted of an effective ingredient (the first component) and the pharmaceutically acceptable excipients (the second component), i.e., sugars or sugar alcohols, can comprise the other additives which can be commonly added in the pharmaceutical field. In the agglomerate unit of the present invention, the said first component is present as discontinuous phase, and the said second component is present as continuous phase. That is, the said second component is present in the form surrounding the first component, in which the first component is surrounded by the second component, simultaneously with forming a separate discontinuous phase. In addition, it is preferable for the first component to uniformly disperse in the second component. When the powder of the present invention comprising such the agglomerate unit is administered to a patient, it is assumed that the patient can not feel the bitterness due to that the second component with sweetness and the first component with bitterness almost concurrently stimulate taste cells of a taste bud, simultaneously with that the bitterness of which the first component constituting the discontinuous phase is dissolved by the second component constituting the continuous phase in the mouth and thus, a rate for sensing the bitterness is delayed instantaneously.

Especially, it is considered as being a very special phenomenon that the effect for masking the bitterness is obtained by taking the internal structure of the agglomerate of the present invention, in light of that the effect for masking the bitterness does not exhibit when the form of agglomerate unit is made into common granular form without segregating the discontinuous and continuous phases like the present invention.

Meanwhile, in order to prepare the agglomerate unit into discontinuous and continuous phases, it is necessary to dissolve the second component in the proper solvent and then disperse the first component into the solution. In this case, the solvent can be the solvent comprising at least one organic solution selected from the group consisting of water, a straight, branched or cyclic chain alcohol having 1 to 4 carbon atoms and a straight, branched or cyclic chain ketone having 3 to 6 carbon atoms, or the mix solution thereof. In the most preferable embodiment, said solvent is water. The composition comprising the agglomerate unit of the present invention can be obtained by dispersing said the first component and then, drying the dispersion obtain, in this case the dry method can be a solvent evaporation method, spray drying or freeze-drying, etc., and any dry method can be used unless the internal structure of the agglomerate unit is constituted by the continuous phase and the discontinuous phase. The composition dried as such is adjusted as a proper size by pulverizing or sieving, and also is mixed with the pharmaceutical acceptable excipient or additive, and thus, is obtained as the microgranule preparation of the present invention.

In addition, a high sweetening agent can be included in the agglomerate unit, for example, the high sweetening agent selected from sucrose, dextrose, fructose, glucose, liquid glucose, maltose saccharin, cyclamate, aspartame K, sucralose, alitame and neotame can be included. Such the high sweetening agent can be comprised in the preparation of the present invention after mixing process, i.e. after mixing the agglomerate unit, and in the case of the effective ingredient with severe bitterness, the effect masking the bitterness can be more superior by constituting such high sweetening agent as the continuous phase.

One or more of the pharmaceutical acceptable flavoring agent can be used so as to improve the flavor of the preparation and to enhance drug compliance. As the acceptable flavoring agent, orange flavor, grape flavor, apple flavor, lemon flavor, strawberry flavor, cherry flavor, pineapple flavor, banana flavor, tutti frutti flavor, blueberry flavor, peppermint flavor, cocoa flavor, peach flavor and milk flavor or the pharmaceutically acceptable flavoring agent and the mixture thereof can be used.

The microgranule preparation obtained by such method has effects that it has a rapid dissolving rate in the mouth, and does not have the aftersensation and feeling irritation in the mouth, together with the effect for masking the bitterness.

The feeling irritation refers to the sensation that a person feels the preparation unpleasant by perceiving it as a foreign substance in the mouth when administering it as mentioned above, according to the research of the inventors of the present application, it can be shown that such feeling irritation is closely related to a microscopic disintegration and a dissolution pattern. That is, in order to reduce the feeling of irritation, it is shown that the disintegration and dissolution should be rightly started in the mouth soon after administering it, and also, rates of the disintegration and dissolution should be very constant in the mouth.

Especially, in order to achieve it, it is shown that it is important not to use a binding agent which was considered as being necessary to use the ordinary granule preparation. Therefore, the present invention has another characteristic feature that the binding agent is not used in dissolving the second component constituting continuous phase and/or the sweetening agent in the solvent, and dispersing the first component into it and drying it. That is, unlike the ordinary granule agent, the internal structure of the agglomerate unit is constituted as the continuous phase and discontinuous phase and thus the disintegration and dissolution are started in a moment in the mouth when administering the preparation, and the rapid and continuous disintegration and dissolution are exhibited during a microscopic section ranging from several seconds~numbers of seconds and thus the new preparation having no feeling irritation is obtained.

In addition, according to the inventor's research of the present application, it is shown that the internal structure of the agglomerate unit affects the feeling of irritation in the mouth, and when the binding agent is not used, since the inert excipient constituting the preparation together with the effective ingredients does not remain in the mouth and moves to gastrointestinal tract in a moment together with a saliva, it is found that any sensation due to the administration of the preparation in the mouth after administering it does not remain.

Especially, the microgranule preparation of the present invention has the characteristic feature that it can be rapidly disintegrated and dissolved in a mouth, and such the characteristic feature is also considered as being the effects which can be obtained by constituting the agglomerate into the continuous phase and discontinuous phase and simultaneously using no binding agent. That is, in the case of the other preparation without water like in the present invention, for example, industrially available ODF or ODT, it remains in the mouth for at least of numbers of second after administering it, but, since the preparation of the present invention is disintegrated and dissolved within several seconds (substantially, almost simultaneously with the administration) and then moved into the gastrointestinal tract, such characteristic feature is very differentiated from the ordinary 'preparation taking without water'.

EMBODIMENT FOR PRACTICING THE INVENTION

Hereinafter, the present invention will be explained with working examples. But, it should be paid attention to that the following examples are not limited the scope of the rights of the present invention as the specific embodiments, and various modifications can be present within the technical idea of the present invention.

Examples 1 to 7

Pharmaceutical compositions comprising the agglomerate units according to the present invention were made by using various effective ingredients. That is, based on the components and the contents as listed in the below Table 1, the second component was dissolved in the solvent, and then the first component was added and dispersed by stirring. After drying the dispersion, the agglomerate unit according to the present invention was obtained. After mixing sugar or sugar alcohol in the state of particle into the agglomerate unit obtained, the pharmaceutical composition according to the present invention was prepared. Also, it was identified as to whether the internal structure of the agglomerate unit exhibits the discontinuous/continuous phases by observing the agglomerate unit obtained.

TABLE 1

| | | Example 1 | Example 2 | Example 3 | Example 4 | Example 5 | Example 6 | Example 7 |
|---|---|---|---|---|---|---|---|---|
| the first component | component | hydrochloric acid donepezil | udenafil | citric acid sildenafil | hydrochloric acid vardenafil | succinic acid sumatriptan | hydrochloric acid dapoxetine | hydrochloric acid ondansetron |
| | the amount used | 10 mg | 100 mg | 70.23 mg | 23.7 mg | 70 mg | 67.2 mg | 8 mg |
| The second component | component | xylitol | xylitol | xylitol | xylitol | xylitol | xylitol | xylitol |
| | the amount used | 250 mg | 250 mg | 250 mg | 250 mg | 250 mg | 250 mg | 250 mg |
| solvent | kinds | purified water | purified water | purified water | purified water | purified water | purified water | purified water |
| | the amount used | 170 mg | 170 mg | 170 mg | 170 mg | 170 mg | 170 mg | 170 mg |
| internal structure | | continuous/ discontinuous phase | continuous/ discontinuous phase | continuous/ discontinuous phase | continuous/ discontinuous phase | continuous/ discontinuous phase | continuous/ discontinuous phase | continuous/ discontinuous phase |
| sugar/sugar alcohol (post-mixing) | kinds | xylitol | xylitol | xylitol | xylitol | xylitol | xylitol | xylitol |
| | the amount used | 210 mg | 120 mg | 149.77 mg | 196.3 mg | 150 mg | 152.8 mg | 212 mg |
| high sweetening agent (post-mixing) | kinds | aspartame | aspartame | aspartame | aspartame | aspartame | aspartame | aspartame |
| | the amount used | 30 mg | 30 mg | 30 mg | 30 mg | 30 mg | 30 mg | 30 mg |
| total mass (solid) | | 500 mg | 500 mg | 500 mg | 500 mg | 500 mg | 500 mg | 500 mg |

Comparative Examples 1 to 7

As corresponding to examples 1 to 7, preparations were made to have the contents listed in the below Table 2, as prepared by the granule preparation method (wet process) of the ordinary technique.

TABLE 2

| | | comparative example 1 | comparative example 2 | comparative example 3 | comparative example 4 | comparative example 5 | comparative example 6 | comparative example 7 |
|---|---|---|---|---|---|---|---|---|
| the first component | component | hydrochloric acid donepezil | udenafil | citric acid sildenafil | hydrochloric acid vardenafil | succinic acid sumatriptan | hydrochloric acid dapoxetine | hydrochloric acid ondansetron |
| | the amount used | 10 mg | 100 mg | 70.23 mg | 23.7 mg | 70 mg | 67.2 mg | 8 mg |
| The second component | component | xylitol | xylitol | xylitol | xylitol | xylitol | xylitol | xylitol |
| | the amount used | 250 mg | 250 mg | 250 mg | 250 mg | 250 mg | 250 mg | 250 mg |
| Binding agent | kinds | polyvinyl pyrrolidone | polyvinyl pyrrolidone | polyvinyl pyrrolidone | polyvinyl pyrrolidone | polyvinyl pyrrolidone | polyvinyl pyrrolidone | polyvinyl pyrrolidone |
| | the amount used | 10 mg | 10 mg | 10 mg | 10 mg | 10 mg | 10 mg | 10 mg |
| Binding agent | kinds | the purified water | the purified water | the purified water | the purified water | the purified water | the purified water | the purified water |
| | the amount used | 200 mg | 200 mg | 200 mg | 200 mg | 200 mg | 200 mg | 200 mg |

TABLE 2-continued

|  |  | comparative example 1 | comparative example 2 | comparative example 3 | comparative example 4 | comparative example 5 | comparative example 6 | comparative example 7 |
|---|---|---|---|---|---|---|---|---|
| internal structure |  | discontinuous/ discontinuous phase | discontinuous/ discontinuous phase | discontinuous/ discontinuous phase | discontinuous/ discontinuous phase | discontinuous/ discontinuous phase | discontinuous/ discontinuous phase | discontinuous/ discontinuous phase |
| sugar/sugar alcohol (post-mixing) | kinds | xylitol | xylitol | xylitol | xylitol | xylitol | xylitol | xylitol |
|  | the amount used | 200 mg | 110 mg | 139.77 mg | 186.3 mg | 140 mg | 142.8 mg | 202 mg |
| high sweetening agent (post-mixing) | kinds | aspartame | aspartame | aspartame | aspartame | aspartame | aspartame | aspartame |
|  | the amount used | 30 mg | 30 mg | 30 mg | 30 mg | 30 mg | 30 mg | 30 mg |
| total mass(solid) |  | 500 mg | 500 mg | 500 mg | 500 mg | 500 mg | 500 mg | 500 mg |

Examples 8 to 14

Pharmaceutical compositions were prepared as the same method as examples 1 to 7, except that the high sweetening agent is included within the continuous phase. That is, when dissolving the second component in the solvent, the high sweetening agent was dissolved together, and then, the first component was dispersed therein and pharmaceutical compositions of the present invention were prepared as the same manner as in examples 1 to 7. The specific contents are listed in the below Table 3.

TABLE 3

|  |  | Example 8 | Example 9 | Example 10 | Example 11 | Example 12 | Example 13 | Example 14 |
|---|---|---|---|---|---|---|---|---|
| the 1st component | component | hydrochloric acid donepezil | udenafil | citric acid sildenafil | hydrochloric acid vardenafil | succinic acid sumatriptan | hydrochloric acid dapoxetine | hydrochloric acid ondansetron |
|  | the amount used | 10 mg | 100 mg | 70.23 mg | 23.7 mg | 70 mg | 67.2 mg | 8 mg |
| The second component | component | xylitol | xylitol | xylitol | xylitol | xylitol | xylitol | xylitol |
|  | the amount used | 250 mg | 250 mg | 250 mg | 250 mg | 250 mg | 250 mg | 250 mg |
| high sweetening agent | component | aspartame | aspartame | aspartame | aspartame | aspartame | aspartame | aspartame |
|  | the amount used | 30 mg | 30 mg | 30 mg | 30 mg | 30 mg | 30 mg | 30 mg |
| solvent | kinds | the purified water | the purified water | the purified water | the purified water | the purified water | the purified water | the purified water |
|  | the amount used | 170 mg | 170 mg | 170 mg | 170 mg | 170 mg | 170 mg | 170 mg |
| internal structure |  | continuous/ discontinuous phase | continuous/ discontinuous phase | continuous/ discontinuous phase | continuous/ discontinuous phase | continuous/ discontinuous phase | continuous/ discontinuous phase | continuous/ discontinuous phase |
| sugar/sugar alcohol (post-mixing) | kinds | xylitol | xylitol | xylitol | xylitol | xylitol | xylitol | xylitol |
|  | the amount used | 210 mg | 120 mg | 149.77 mg | 196.3 mg | 150 mg | 152.8 mg | 212 mg |
| total mass(solid) |  | 500 mg | 500 mg | 500 mg | 500 mg | 500 mg | 500 mg | 500 mg |

Experiment 1: Identification of the Effect for Masking Bitterness

Sensory test by twenty (20) healthy adults were practiced for bitterness regarding to the pharmaceutical composition prepared in the above examples 1 to 14 and comparative examples 1 to 7. The results were estimated according to the below evaluation criteria and then were represented. In this case, a blind-test was keep for the test subjects in all tests.

Score 0: No bitterness
Score 1: No rarely bitterness
Score 2: A little bitterness
Score 3: Present bitterness
Score 4: Very severe bitterness A result tables scored by the respective subjects are represented in the below Tables 4 to 6.

TABLE 4

|  | | Example | | | | | | |
|---|---|---|---|---|---|---|---|---|
|  | | Example 1 | Example 2 | Example 3 | Example 4 | Example 5 | Example 6 | Example 7 |
| subject score | | 0 | 0 | 2 | 2 | 2 | 1 | 2 |
| | | 0 | 1 | 2 | 0 | 0 | 1 | 2 |
| | | 0 | 1 | 0 | 2 | 0 | 1 | 0 |
| | | 0 | 2 | 1 | 1 | 2 | 2 | 2 |
| | | 0 | 0 | 1 | 1 | 1 | 2 | 1 |
| | | 1 | 1 | 2 | 1 | 2 | 1 | 0 |
| | | 1 | 1 | 1 | 0 | 1 | 0 | 2 |
| | | 2 | 2 | 2 | 0 | 0 | 0 | 1 |
| | | 2 | 1 | 2 | 1 | 2 | 1 | 2 |
| | | 0 | 1 | 0 | 2 | 2 | 2 | 2 |
| | | 1 | 2 | 1 | 0 | 2 | 1 | 2 |
| | | 0 | 0 | 0 | 0 | 2 | 0 | 1 |
| | | 2 | 0 | 2 | 2 | 2 | 2 | 1 |
| | | 0 | 2 | 0 | 2 | 2 | 2 | 2 |
| | | 1 | 1 | 1 | 1 | 2 | 1 | 1 |
| | | 1 | 1 | 0 | 0 | 1 | 1 | 0 |
| | | 1 | 2 | 2 | 2 | 0 | 1 | 1 |
| | | 0 | 0 | 1 | 2 | 1 | 1 | 0 |
| | | 0 | 0 | 0 | 0 | 0 | 2 | 1 |
| | | 1 | 0 | 1 | 1 | 2 | 2 | 0 |
| average | | 0.7 | 0.9 | 1.1 | 1.0 | 1.3 | 1.2 | 1.2 |

TABLE 5

|  | | Example | | | | | | |
|---|---|---|---|---|---|---|---|---|
|  | | Example 8 | Example 9 | Example 10 | Example 11 | Example 12 | Example 13 | Example 14 |
| subject score | | 0 | 0 | 1 | 1 | 1 | 1 | 1 |
| | | 0 | 0 | 1 | 1 | 0 | 1 | 1 |
| | | 0 | 0 | 0 | 1 | 1 | 0 | 1 |
| | | 0 | 0 | 1 | 1 | 0 | 0 | 0 |
| | | 0 | 0 | 0 | 1 | 1 | 1 | 0 |
| | | 0 | 0 | 0 | 0 | 0 | 1 | 1 |
| | | 1 | 1 | 1 | 1 | 0 | 0 | 1 |
| | | 1 | 1 | 0 | 0 | 0 | 0 | 0 |
| | | 0 | 0 | 1 | 1 | 0 | 0 | 1 |
| | | 1 | 0 | 1 | 0 | 0 | 0 | 0 |
| | | 1 | 1 | 1 | 0 | 0 | 1 | 1 |
| | | 1 | 1 | 0 | 0 | 0 | 0 | 0 |
| | | 1 | 1 | 0 | 1 | 1 | 1 | 0 |
| | | 1 | 1 | 0 | 0 | 0 | 0 | 1 |
| | | 0 | 1 | 1 | 0 | 1 | 1 | 0 |
| | | 1 | 0 | 1 | 0 | 1 | 1 | 0 |
| | | 1 | 0 | 1 | 1 | 0 | 1 | 0 |
| | | 0 | 1 | 1 | 1 | 1 | 1 | 0 |
| | | 0 | 0 | 1 | 1 | 0 | 1 | 1 |
| | | 1 | 1 | 0 | 1 | 0 | 0 | 0 |
| average | | 0.5 | 0.5 | 0.6 | 0.6 | 0.4 | 0.6 | 0.5 |

TABLE 6

| | comparative example 1 | comparative example 2 | comparative example 3 | comparative example 4 | comparative example 5 | comparative example 6 | comparative example 7 |
|---|---|---|---|---|---|---|---|
| Subject score | 4 | 3 | 3 | 3 | 4 | 3 | 3 |
| | 4 | 4 | 3 | 3 | 4 | 4 | 4 |
| | 4 | 4 | 3 | 3 | 3 | 4 | 4 |
| | 4 | 3 | 3 | 3 | 4 | 4 | 4 |
| | 3 | 4 | 3 | 4 | 3 | 3 | 4 |
| | 3 | 4 | 4 | 4 | 3 | 4 | 3 |
| | 4 | 3 | 4 | 4 | 3 | 3 | 3 |
| | 3 | 3 | 4 | 3 | 3 | 4 | 4 |
| | 4 | 3 | 4 | 3 | 4 | 4 | 4 |
| | 3 | 4 | 3 | 4 | 4 | 3 | 4 |
| | 3 | 3 | 4 | 3 | 4 | 3 | 3 |
| | 4 | 3 | 4 | 4 | 3 | 3 | 3 |
| | 3 | 4 | 4 | 4 | 4 | 3 | 3 |
| | 4 | 3 | 3 | 3 | 4 | 4 | 4 |
| | 4 | 3 | 4 | 4 | 3 | 3 | 4 |
| | 4 | 3 | 4 | 4 | 3 | 3 | 3 |
| | 3 | 4 | 3 | 3 | 3 | 4 | 4 |
| | 4 | 4 | 3 | 4 | 3 | 3 | 4 |
| | 3 | 3 | 4 | 4 | 4 | 3 | 3 |
| | 4 | 3 | 3 | 3 | 3 | 4 | 3 |
| Average | 3.6 | 3.4 | 3.5 | 3.5 | 3.5 | 3.5 | 3.6 |

Based on the above Tables 4 to 6, when determining significance via t-test for the same main components of examples and comparative examples, the results of Tables 7 and 8 were obtained. That is, it was verified that all of examples 1 to 7 and examples 8 to 14 represent differences having the statistical significances.

TABLE 7

| Example 1 vs comparative example 1 | Example 2 vs comparative example 2 | Example 3 vs comparative example 3 | Example 4 vs comparative example 4 | Example 5 vs comparative example 5 | Example 6 vs comparative example 6 | Example 7 vs comparative example 7 |
|---|---|---|---|---|---|---|
| $p < 0.001$ | $p < 0.001$ | $p < 0.001$ | $p < 0.001$ | $p < 0.001$ | $p < 0.001$ | $p < 0.001$ |

TABLE 8

| Example 8 vs comparative example 1 | Example 9 vs comparative example 2 | Example 10 vs comparative example 3 | Example 11 vs comparative example 4 | Example 12 vs comparative example 5 | Example 13 vs comparative example 6 | Example 14 vs comparative example 7 |
|---|---|---|---|---|---|---|
| $p < 0.001$ | $p < 0.001$ | $p < 0.001$ | $p < 0.001$ | $p < 0.001$ | $p < 0.001$ | $p < 0.001$ |

Experiment 2: Experiment for Feeling of Irritation in a Mouth

Sensory test by twenty (20) healthy adults were practiced for feeling of irritation regarding to the pharmaceutical compositions prepared in the above examples 1 to 14 and comparative examples 1 to 7. The results were estimated according to the below evaluation criteria and then the result were determined. In this case, a blind-test was keep for the test subjects in all tests.
  Score 0: No feeling of irritation
  Score 1: No rarely feeling of irritation
  Score 2: A little feeling of irritation
  Score 3: Presence for feeling of irritation
  Score 4: Very severe feeling of irritation
A result tables scored by the respective subjects are represented in the below Tables 9 to 11.

TABLE 9

| | Example 1 | Example 2 | Example 3 | Example 4 | Example 5 | Example 6 | Example 7 |
|---|---|---|---|---|---|---|---|
| subject score | 0 | 1 | 0 | 1 | 0 | 0 | 0 |
| | 1 | 1 | 0 | 0 | 1 | 1 | 1 |
| | 0 | 1 | 0 | 0 | 0 | 1 | 1 |
| | 0 | 1 | 0 | 1 | 0 | 0 | 0 |
| | 1 | 0 | 1 | 1 | 0 | 1 | 0 |
| | 0 | 1 | 1 | 1 | 1 | 0 | 0 |
| | 1 | 1 | 0 | 0 | 0 | 1 | 1 |
| | 0 | 0 | 1 | 1 | 0 | 1 | 0 |
| | 1 | 1 | 0 | 1 | 1 | 0 | 0 |
| | 0 | 0 | 1 | 1 | 0 | 0 | 0 |
| | 1 | 0 | 1 | 0 | 0 | 0 | 0 |
| | 1 | 1 | 0 | 0 | 0 | 0 | 1 |
| | 0 | 1 | 1 | 1 | 0 | 0 | 1 |

TABLE 9-continued

| | Example | | | | | | |
|---|---|---|---|---|---|---|---|
| | Example 1 | Example 2 | Example 3 | Example 4 | Example 5 | Example 6 | Example 7 |
| | 1 | 1 | 0 | 0 | 1 | 0 | 0 |
| | 1 | 1 | 1 | 1 | 1 | 0 | 1 |
| | 1 | 0 | 1 | 1 | 1 | 1 | 0 |
| | 1 | 1 | 0 | 1 | 1 | 0 | 1 |
| | 1 | 1 | 0 | 0 | 1 | 1 | 1 |
| | 1 | 0 | 1 | 1 | 0 | 0 | 1 |
| | 0 | 0 | 1 | 0 | 0 | 0 | 1 |
| average | 0.6 | 0.7 | 0.5 | 0.6 | 0.4 | 0.4 | 0.5 |

TABLE 10

| | Example | | | | | | |
|---|---|---|---|---|---|---|---|
| | Example 8 | Example 9 | Example 10 | Example 11 | Example 12 | Example 13 | Example 14 |
| Subject score | 0 | 1 | 1 | 1 | 1 | 0 | 1 |
| | 0 | 0 | 1 | 1 | 0 | 0 | 0 |
| | 0 | 0 | 1 | 1 | 0 | 1 | 0 |
| | 1 | 0 | 0 | 1 | 1 | 0 | 1 |
| | 0 | 1 | 1 | 0 | 0 | 0 | 1 |
| | 1 | 0 | 0 | 1 | 1 | 1 | 0 |
| | 1 | 1 | 0 | 0 | 1 | 0 | 1 |
| | 1 | 0 | 0 | 1 | 0 | 0 | 0 |
| | 1 | 1 | 0 | 1 | 0 | 1 | 0 |
| | 0 | 1 | 1 | 0 | 0 | 0 | 1 |
| | 0 | 1 | 0 | 1 | 1 | 1 | 0 |
| | 1 | 1 | 1 | 1 | 1 | 0 | 1 |
| | 1 | 0 | 1 | 0 | 0 | 0 | 1 |
| | 0 | 0 | 1 | 0 | 1 | 1 | 1 |
| | 1 | 0 | 1 | 0 | 1 | 1 | 1 |
| | 0 | 1 | 0 | 0 | 0 | 1 | 0 |
| | 0 | 1 | 1 | 0 | 0 | 1 | 1 |
| | 0 | 0 | 1 | 0 | 1 | 0 | 1 |
| | 0 | 0 | 0 | 0 | 0 | 1 | 0 |
| | 1 | 1 | 1 | 0 | 0 | 0 | 1 |
| average | 0.5 | 0.6 | 0.6 | 0.5 | 0.4 | 0.5 | 0.6 |

TABLE 11

| | comparative example | | | | | | |
|---|---|---|---|---|---|---|---|
| | comparative example 1 | comparative example 2 | comparative example 3 | comparative example 4 | comparative example 5 | comparative example 6 | comparative example 7 |
| Subject score | 2 | 2 | 2 | 2 | 3 | 2 | 1 |
| | 2 | 2 | 3 | 1 | 3 | 3 | 1 |
| | 1 | 1 | 1 | 3 | 3 | 2 | 3 |
| | 2 | 3 | 2 | 3 | 3 | 3 | 1 |
| | 3 | 3 | 3 | 3 | 1 | 2 | 3 |
| | 1 | 3 | 2 | 3 | 3 | 2 | 2 |
| | 3 | 1 | 3 | 3 | 2 | 2 | 1 |
| | 1 | 3 | 3 | 2 | 1 | 2 | 3 |
| | 3 | 2 | 2 | 2 | 2 | 2 | 3 |
| | 2 | 2 | 3 | 2 | 1 | 3 | 2 |
| | 3 | 2 | 1 | 1 | 2 | 2 | 3 |
| | 1 | 1 | 3 | 3 | 1 | 2 | 3 |
| | 1 | 1 | 3 | 2 | 3 | 3 | 1 |
| | 2 | 3 | 3 | 2 | 3 | 1 | 3 |
| | 1 | 2 | 1 | 1 | 3 | 3 | 2 |
| | 3 | 2 | 1 | 1 | 3 | 3 | 1 |
| | 2 | 3 | 1 | 3 | 3 | 1 | 3 |
| | 3 | 1 | 3 | 2 | 2 | 3 | 2 |
| | 2 | 1 | 1 | 3 | 2 | 2 | 2 |
| | 3 | 2 | 3 | 1 | 3 | 1 | 3 |
| average | 2.1 | 2.0 | 2.2 | 2.2 | 2.4 | 2.2 | 2.2 |

Based on the above Tables 9 to 11, when determining significance via t-test for the same main components of examples and comparative examples, the results of Tables 12 and 13 were obtained. That is, it was verified that all of examples 1 to 7 and examples 8 to 14 represent differences having the statistical significances with comparative examples 1 to 7.

TABLE 12

| Example 1 vs comparative example 1 | Example 2 vs comparative example 2 | Example 3 vs comparative example 3 | Example 4 vs comparative example 4 | Example 5 vs comparative example 5 | Example 6 vs comparative example 6 | Example 7 vs comparative example 7 |
|---|---|---|---|---|---|---|
| $p < 0.001$ | $p < 0.001$ | $p < 0.001$ | $p < 0.001$ | $p < 0.001$ | $p < 0.001$ | $p < 0.001$ |

TABLE 13

| Example 8 vs comparative example 1 | Example 9 vs comparative example 2 | Example 10 vs comparative example 3 | Example 11 vs comparative example 4 | Example 12 vs comparative example 5 | Example 13 vs comparative example 6 | Example 14 vs comparative example 7 |
|---|---|---|---|---|---|---|
| p < 0.001 | p < 0.001 | p < 0.001 | p < 0.001 | p < 0.001 | p < 0.001 | p < 0.001 |

Experiment 3: Experiment for Aftersensation in a Mouth

Sensory test by twenty (20) healthy adults were practiced for aftersensation in a mouth regarding to the pharmaceutical compositions prepared in the above examples 1 to 14 and comparative examples 1 to 7. The results were estimated according to the below evaluation criteria and then the result were determined. In this case, a blind-test was keep for the test subjects in all tests.

Score 0: No aftersensation
Score 1: No rarely aftersensation
Score 2: A little aftersensation
Score 3: Present aftersensation
Score 4: Very severe aftersensation A result tables scored by the respective subjects are represented in the below Tables 14 to 16.

TABLE 14

| | Example | | | | | | |
|---|---|---|---|---|---|---|---|
| | Example 1 | Example 2 | Example 3 | Example 4 | Example 5 | Example 6 | Example 7 |
| Subject score | 1 | 1 | 0 | 0 | 0 | 1 | 0 |
| | 1 | 0 | 0 | 1 | 0 | 1 | 0 |
| | 1 | 1 | 0 | 1 | 1 | 0 | 0 |
| | 0 | 0 | 0 | 1 | 1 | 1 | 0 |
| | 0 | 1 | 1 | 0 | 0 | 1 | 1 |
| | 1 | 1 | 0 | 1 | 1 | 1 | 0 |
| | 0 | 1 | 0 | 0 | 1 | 1 | 1 |
| | 0 | 0 | 1 | 0 | 1 | 1 | 0 |
| | 1 | 1 | 1 | 1 | 1 | 1 | 1 |
| | 0 | 0 | 0 | 0 | 1 | 1 | 1 |
| | 1 | 0 | 1 | 1 | 0 | 1 | 0 |
| | 1 | 0 | 1 | 1 | 1 | 1 | 0 |
| | 1 | 1 | 1 | 0 | 0 | 1 | 1 |
| | 1 | 1 | 1 | 0 | 1 | 0 | 1 |
| | 0 | 1 | 1 | 1 | 0 | 1 | 0 |
| | 0 | 0 | 1 | 1 | 0 | 1 | 1 |
| | 0 | 0 | 1 | 1 | 1 | 0 | 0 |
| | 0 | 0 | 1 | 0 | 0 | 0 | 0 |
| | 1 | 1 | 1 | 1 | 1 | 1 | 0 |
| | 0 | 0 | 0 | 1 | 0 | 1 | 0 |
| Average | 0.5 | 0.5 | 0.6 | 0.6 | 0.6 | 0.8 | 0.4 |

TABLE 15

| | Example | | | | | | |
|---|---|---|---|---|---|---|---|
| | Example 8 | Example 9 | Example 10 | Example 11 | Example 12 | Example 13 | Example 14 |
| subject score | 0 | 1 | 1 | 1 | 0 | 1 | 1 |
| | 1 | 0 | 1 | 1 | 0 | 0 | 0 |
| | 0 | 0 | 1 | 0 | 0 | 1 | 1 |
| | 0 | 1 | 1 | 1 | 0 | 1 | 1 |
| | 0 | 0 | 0 | 1 | 1 | 0 | 1 |
| | 0 | 1 | 0 | 1 | 0 | 1 | 1 |
| | 0 | 0 | 1 | 0 | 0 | 1 | 0 |
| | 0 | 1 | 1 | 1 | 1 | 1 | 0 |
| | 1 | 0 | 0 | 1 | 0 | 1 | 1 |
| | 1 | 0 | 1 | 1 | 0 | 1 | 1 |
| | 1 | 0 | 0 | 0 | 1 | 0 | 0 |
| | 1 | 1 | 0 | 0 | 0 | 0 | 0 |
| | 0 | 0 | 0 | 0 | 1 | 0 | 1 |
| | 1 | 0 | 0 | 0 | 0 | 1 | 0 |
| | 1 | 0 | 0 | 0 | 1 | 0 | 1 |
| | 0 | 1 | 1 | 0 | 0 | 1 | 1 |
| | 1 | 0 | 0 | 1 | 0 | 1 | 0 |
| | 1 | 1 | 0 | 0 | 0 | 1 | 0 |
| | 0 | 1 | 0 | 1 | 0 | 1 | 0 |
| | 0 | 0 | 0 | 1 | 1 | 0 | 0 |
| Average | 0.4 | 0.4 | 0.4 | 0.6 | 0.3 | 0.7 | 0.5 |

TABLE 16

| | comparative example | | | | | | |
|---|---|---|---|---|---|---|---|
| | comparative example 1 | comparative example 2 | comparative example 3 | comparative example 4 | comparative example 5 | comparative example 6 | comparative Example 7 |
| Subject score | 3 | 3 | 3 | 1 | 1 | 3 | 2 |
| | 2 | 2 | 1 | 3 | 3 | 2 | 2 |
| | 2 | 2 | 3 | 2 | 3 | 1 | 1 |
| | 2 | 3 | 1 | 2 | 2 | 3 | 3 |
| | 3 | 3 | 2 | 1 | 2 | 2 | 2 |
| | 3 | 1 | 1 | 1 | 2 | 3 | 2 |
| | 1 | 3 | 2 | 2 | 1 | 3 | 2 |
| | 2 | 1 | 1 | 1 | 2 | 2 | 2 |
| | 3 | 2 | 2 | 2 | 3 | 2 | 2 |
| | 2 | 3 | 3 | 2 | 3 | 1 | 2 |
| | 2 | 2 | 2 | 3 | 2 | 1 | 3 |
| | 2 | 1 | 1 | 3 | 3 | 1 | 3 |
| | 2 | 1 | 2 | 1 | 3 | 1 | 1 |
| | 1 | 1 | 2 | 1 | 2 | 2 | 3 |
| | 2 | 1 | 2 | 1 | 3 | 3 | 2 |
| | 1 | 1 | 1 | 1 | 1 | 1 | 2 |

TABLE 16-continued

| | comparative example | | | | | | |
|---|---|---|---|---|---|---|---|
| | comparative example 1 | comparative example 2 | comparative example 3 | comparative example 4 | comparative example 5 | comparative example 6 | comparative Example 7 |
| | 1 | 3 | 2 | 1 | 3 | 3 | 1 |
| | 1 | 3 | 1 | 3 | 2 | 2 | 2 |
| | 1 | 3 | 2 | 2 | 1 | 2 | 1 |
| | 1 | 2 | 2 | 3 | 3 | 2 | 2 |
| Average | 1.9 | 2.1 | 1.8 | 1.8 | 2.3 | 2.0 | 2.0 |

Based on the above Tables 14 to 16, when determining significance via t-test for the same main components of examples and comparative examples, the results of Tables 17 and 18 were obtained. That is, it was verified that all of examples 1 to 7 and examples 8 to 14 represent differences having the statistical significances with comparative examples 1 to 7.

TABLE 17

| Example 1 vs comparative example 1 | Example 2 vs comparative example 2 | Example 3 vs comparative example 3 | Example 4 vs comparative example 4 | Example 5 vs comparative example 5 | Example 6 vs comparative example 6 | Example 7 vs comparative example 7 |
|---|---|---|---|---|---|---|
| $p < 0.001$ | $p < 0.001$ | $p < 0.001$ | $p < 0.001$ | $p < 0.001$ | $p < 0.001$ | $p < 0.001$ |

TABLE 18

| Example 8 vs comparative example 1 | Example 9 vs comparative example 2 | Example 10 vs comparative example 3 | Example 11 vs comparative example 4 | Example 12 vs comparative example 5 | Example 13 vs comparative example 6 | Example 14 vs comparative example 7 |
|---|---|---|---|---|---|---|
| $p < 0.001$ | $p < 0.001$ | $p < 0.001$ | $p < 0.001$ | $p < 0.001$ | $p < 0.001$ | $p < 0.001$ |

Experiment 4: Test for the Dissolution Time in a Mouth

The test for the dissolution time in a mouth by twenty (20) healthy adults were practiced for the pharmaceutical compositions prepared in the above examples 1 to 14 and comparative examples 1 to 7. The dissolution time in the mouth was determined by using a stopwatch a duration for from the administration time to complete dissolution time. In this case, a blind-test was keep for the test subjects in all tests.

TABLE 19

| | | Example | | | | | |
|---|---|---|---|---|---|---|---|
| | | Example 1 | Example 2 | Example 3 | Example 4 | Example 5 | Example 6 | Example 7 |
| subject determination results | | 4 | 8 | 4 | 7 | 3 | 6 | 6 |
| | | 6 | 8 | 6 | 5 | 3 | 4 | 4 |
| | | 3 | 3 | 4 | 8 | 6 | 3 | 3 |
| | | 3 | 3 | 4 | 7 | 3 | 4 | 7 |
| | | 8 | 4 | 6 | 8 | 6 | 7 | 6 |
| | | 3 | 3 | 5 | 4 | 5 | 8 | 6 |
| | | 7 | 6 | 6 | 3 | 5 | 8 | 8 |
| | | 6 | 4 | 6 | 7 | 8 | 8 | 5 |
| | | 5 | 3 | 7 | 7 | 5 | 6 | 4 |
| | | 3 | 5 | 7 | 4 | 7 | 8 | 5 |
| | | 6 | 7 | 6 | 8 | 7 | 3 | 7 |
| | | 5 | 8 | 3 | 8 | 8 | 7 | 6 |
| | | 8 | 3 | 6 | 3 | 8 | 3 | 5 |
| | | 3 | 8 | 8 | 3 | 3 | 3 | 6 |
| | | 8 | 8 | 5 | 6 | 6 | 3 | 5 |
| | | 4 | 8 | 4 | 4 | 3 | 6 | 5 |
| | | 6 | 5 | 6 | 7 | 6 | 3 | 3 |
| | | 3 | 5 | 3 | 3 | 7 | 6 | 4 |
| | | 3 | 4 | 7 | 8 | 7 | 7 | 4 |
| | | 6 | 7 | 4 | 4 | 4 | 6 | 5 |
| average | | 5.0 | 5.5 | 5.4 | 5.7 | 5.5 | 5.5 | 5.2 |

TABLE 20

| | Example | | | | | | |
|---|---|---|---|---|---|---|---|
| | Example 8 | Example 9 | Example 10 | Example 11 | Example 12 | Example 13 | Example 14 |
| subject determination results | 5 | 5 | 7 | 3 | 3 | 5 | 8 |
| | 8 | 5 | 7 | 8 | 7 | 5 | 5 |
| | 8 | 3 | 5 | 8 | 7 | 8 | 4 |
| | 4 | 5 | 9 | 9 | 7 | 3 | 7 |
| | 7 | 8 | 6 | 4 | 4 | 6 | 6 |
| | 6 | 3 | 9 | 5 | 8 | 6 | 7 |
| | 9 | 4 | 6 | 6 | 9 | 6 | 7 |
| | 3 | 6 | 9 | 9 | 9 | 3 | 6 |
| | 5 | 5 | 5 | 9 | 7 | 7 | 6 |
| | 4 | 4 | 7 | 4 | 6 | 3 | 9 |
| | 4 | 3 | 6 | 6 | 4 | 6 | 7 |
| | 3 | 4 | 3 | 6 | 7 | 8 | 8 |
| | 3 | 3 | 6 | 5 | 4 | 7 | 8 |
| | 3 | 5 | 6 | 6 | 4 | 6 | 5 |
| | 5 | 3 | 5 | 7 | 9 | 9 | 9 |
| | 6 | 4 | 5 | 9 | 4 | 3 | 6 |
| | 5 | 3 | 7 | 9 | 6 | 5 | 7 |
| | 4 | 7 | 4 | 6 | 9 | 6 | 9 |
| | 8 | 5 | 9 | 4 | 4 | 4 | 8 |
| | 6 | 4 | 9 | 9 | 9 | 9 | 8 |
| average | 5.3 | 4.5 | 6.5 | 6.6 | 6.4 | 5.8 | 7.0 |

TABLE 21

| | comparative example | | | | | | |
|---|---|---|---|---|---|---|---|
| | comparative example 1 | comparative example 2 | comparative example 3 | comparative example 4 | comparative example 5 | comparative example 6 | comparative Example 7 |
| subject determination results | 17 | 21 | 20 | 21 | 25 | 25 | 26 |
| | 17 | 18 | 22 | 18 | 16 | 21 | 25 |
| | 22 | 21 | 19 | 25 | 22 | 29 | 21 |
| | 25 | 18 | 22 | 25 | 24 | 17 | 24 |
| | 27 | 21 | 24 | 20 | 24 | 23 | 29 |
| | 22 | 15 | 28 | 24 | 29 | 28 | 24 |
| | 18 | 18 | 25 | 19 | 25 | 17 | 20 |
| | 24 | 17 | 26 | 30 | 28 | 29 | 15 |
| | 24 | 24 | 24 | 21 | 24 | 25 | 21 |
| | 28 | 30 | 16 | 20 | 28 | 18 | 26 |
| | 26 | 26 | 30 | 20 | 25 | 22 | 30 |
| | 18 | 22 | 30 | 25 | 26 | 15 | 25 |
| | 19 | 30 | 21 | 22 | 21 | 21 | 15 |
| | 25 | 28 | 18 | 28 | 28 | 30 | 25 |
| | 29 | 16 | 17 | 15 | 24 | 30 | 23 |
| | 26 | 26 | 27 | 28 | 24 | 20 | 24 |
| | 17 | 28 | 17 | 27 | 26 | 29 | 25 |
| | 30 | 21 | 25 | 28 | 20 | 17 | 23 |
| | 19 | 28 | 25 | 19 | 17 | 16 | 29 |
| | 18 | 18 | 25 | 26 | 16 | 15 | 22 |
| average | 22.6 | 22.3 | 23.1 | 23.1 | 23.6 | 22.4 | 23.6 |

Based on the above Tables 19 to 21, when determining significance via t-test for the same main components of examples and comparative examples, the results of Tables 22 and 23 were obtained. That is, it was verified that all of examples 1 to 7 and examples 8 to 14 represent differences having the statistical significances with comparative examples 1 to 7.

TABLE 22

| Example 1 vs comparative example 1 | Example 2 vs comparative example 2 | Example 3 vs comparative example 3 | Example 4 vs comparative example 4 | Example 5 vs comparative example 5 | Example 6 vs comparative example 6 | Example 7 vs comparative example 7 |
|---|---|---|---|---|---|---|
| p < 0.001 | p < 0.001 | p < 0.001 | p < 0.001 | p < 0.001 | p < 0.001 | p < 0.001 |

TABLE 23

| Example 8 vs comparative example 1 | Example 9 vs comparative example 2 | Example 10 vs comparative example 3 | Example 11 vs comparative example 4 | Example 12 vs comparative example 5 | Example 13 vs comparative example 6 | Example 14 vs comparative example 7 |
|---|---|---|---|---|---|---|
| $p < 0.001$ | $p < 0.001$ | $p < 0.001$ | $p < 0.001$ | $p < 0.001$ | $p < 0.001$ | $p < 0.001$ |

INDUSTRIAL APPLICABILITY

The microgranule preparation of the present invention is new preparation which does not have feeling of irritation and aftersensation, and is rapidly disintegrated and dissolved in the mouth, as the preparation in which the masking bitterness of effective ingredients having bitterness is regulated by the internal structure of the agglomerated unit. Especially, the preparation of the present invention can achieve the effect of the invention regardless of the kinds of the effective ingredients, and thus can apply to various effective ingredients. In addition, since the preparation process is relatively simple, the high efficient process can be achieved with an expensive cost.

What is claimed is:

1. A method for preparing a pharmaceutical composition comprising agglomerate units consisting of a discontinuous phase consisting of a drug and a continuous phase comprising a sugar or sugar alcohol selected from the group consisting of xylitol, mannitol, isomalt, sorbitol, maltitol, refined white sugar, lactose, inositol, erythritol, crystal fructose, trehalose, ribitol, arabitol, galatitol, lactitol, and maltotritol; and a pharmaceutically acceptable excipient, the method comprising:
    dissolving all or part of the sugar or sugar alcohol in water;
    obtaining a dispersion by dispersing the drug in the water wherein said all or part of the sugar or sugar alcohol is dissolved; and
    obtaining an agglomerate unit by drying the solvent,
    wherein a binding agent is not used in obtaining the agglomerate unit.

2. The method of claim 1, wherein the method further comprises dispersing a high sweeting agent with the drug in water.

3. The method of claim 2, wherein the high sweetening agent is present within the continuous phase.

4. The method of claim 3, wherein the high sweetening agent is selected from the group consisting of sucrose, dextrose, fructose, glucose, liquid glucose, maltose, saccharin, cyclamate, aspartame, acesulpham K, sucralose, alitame, and neotame.

* * * * *